United States Patent
Athanassiadis

(10) Patent No.: US 9,662,278 B2
(45) Date of Patent: May 30, 2017

(54) SLOW RELEASE ENDODONTIC PASTE

(71) Applicant: Matthew Athanassiadis, Redwood Park (AU)

(72) Inventor: Matthew Athanassiadis, Redwood Park (AU)

(*) Notice: Subject to any disclaimer, the term of this patent is extended or adjusted under 35 U.S.C. 154(b) by 0 days.

(21) Appl. No.: 14/765,000

(22) PCT Filed: Jan. 31, 2014

(86) PCT No.: PCT/AU2014/000062
§ 371 (c)(1),
(2) Date: Jul. 31, 2015

(87) PCT Pub. No.: WO2014/117218
PCT Pub. Date: Aug. 7, 2014

(65) Prior Publication Data
US 2016/0030295 A1    Feb. 4, 2016

(30) Foreign Application Priority Data

Jan. 31, 2013 (AU) ................ 2013900307

(51) Int. Cl.
| | |
|---|---|
| *A61K 6/00* | (2006.01) |
| *A61K 31/56* | (2006.01) |
| *A61K 6/02* | (2006.01) |
| *A61K 6/06* | (2006.01) |
| *A61K 31/00* | (2006.01) |

(52) U.S. Cl.
CPC .......... *A61K 6/0035* (2013.01); *A61K 6/0038* (2013.01); *A61K 6/0067* (2013.01); *A61K 6/0205* (2013.01); *A61K 6/0625* (2013.01); *A61K 6/0662* (2013.01); *A61K 31/00* (2013.01); *A61K 31/56* (2013.01)

(58) Field of Classification Search
CPC ...................................... A61K 6/0035
USPC ........................................ 514/169
See application file for complete search history.

(56) References Cited

FOREIGN PATENT DOCUMENTS

| | | |
|---|---|---|
| WO | 2007041768 | 4/2007 |
| WO | 2008102214 | 8/2008 |

OTHER PUBLICATIONS

B Anthanassiadis, et al., pp. 141-146; An in vitro study of the antimicrobial activity of some endodontic medicaments and their bases using an agar well diffusion assay.
Irish Medicines Board; 6 Pgs.; Summary of Product Characteristics; Aug. 12, 2011.

*Primary Examiner* — Taofiq A Solola
(74) *Attorney, Agent, or Firm* — Renner Kenner Greive Bobak Taylor & Weber

(57) ABSTRACT

The present invention discloses a root canal dental paste that has include a first portion made from at least one antibiotic compound and partially set calcium based cement which forms a matrix to at least partially encapsulate the antibiotic compound. The first portion is then ground and combined with a second portion being a non-setting material and an antibiotic to form a paste.

3 Claims, No Drawings

SLOW RELEASE ENDODONTIC PASTE

FIELD OF INVENTION

The field of the invention relates to preparations and formulations used in the dental field, and in particular in root canal therapy.

DESCRIPTION

Root canal surgery is a widely performed operation in which the infected or partially infected pulp material inside a tooth is removed. This entails removal of the nerve tissues and blood vessels (a pulpectomy), and then cleaning and shaping of the resultant hollow that is formed in the tooth.

Once the pulpectomy is completed the remaining space needs to be filled with an inert material and then sealed closed.

Two distinct main groups of endodontic dressings exist. The first is based on calcium hydroxide and the second is based on an antibiotic/steroid combination. The calcium hydroxide-based endodontic dressings have the advantage of being active against bacteria in biofilm form. The antibiotic/steroid combination pastes are generally not as effective against bacteria in biofilms but they are superior to the calcium hydroxide groups in terms of anti-inflammatory properties and generally in biocompatibility.

The vitality of the periodontal ligament is often compromised in teeth that have suffered trauma. If the periodontal ligament has exceeded its biological capacity to repair and becomes devitalised then the tooth in most cases fuses to the alveolar bone commonly referred to as ankylosis and over time the tooth may undergo replacement resorption. This process leads to the eventual loss of the tooth.

Calcium hydroxide pastes are not the treatment of first choice in compromised teeth. The reason for this is that the vitality of the periodontal ligament may be further compromised by the non-specific cytotoxicity that calcium hydroxide pastes exhibit. And which is responsible for its antibacterial properties.

Calcium hydroxide pastes exhibit high levels of non-specific cytotoxicity, which is also the main mode of their antibacterial properties. It all arises from its properties of being alkaline with a pH of 12.5 in an aqueous solution along with low solubility which gives its long period of action.

Antibiotic/steroid pastes are in general less cytotoxic and the steroid component assists in reducing the inflammatory response. The reduction in the inflammatory response is critical as it reduces any collateral damage to the periodontal ligament.

The purpose of the antibiotic component of the paste is to control any bacterial growth within the paste. The loss of the antibiotic results in the ability of the paste to be colonised by bacteria. This occurs after a period of a few days to a few weeks depending on the rate of diffusion of the antibiotic from the paste into the surrounding tissues.

The current antibiotic/steroid pastes utilise zinc oxide as the inert non-setting filling material to make up the bulk of the paste. Zinc oxide has been utilised for decades In immature teeth, which have been traumatised or have been devitalised, it is often the case that root formation is incomplete. In order to complete root formation it is common to rely on subsequent dressings of calcium hydroxide to provide additional calcium ions for the formation of hard tissue to assist in completing the root in addition to an alkaline environment for hard tissue formation. Calcium hydroxide however is highly cytotoxic which is counterintuitive to its purpose as it can compromise the vitality of any remaining vital cells in the tooths' periodontal ligament

OBJECT OF INVENTION

It is an object of the present invention to provide a dental antibiotic/steroid paste that retains its antibacterial properties and osteogenic properties (encouraging bone repair or formation over a longer period. The invention provides a source of calcium to a similar level as traditional calcium hydroxide pastes whilst maintaining a reduced level of cytotoxicity so as not to further compromise the vitality of periodontal ligament cells.

It is an object of the present invention to overcome, or at least substantially ameliorate, the disadvantages of the prior art. No product on the market for over 50 years has ever been designed or developed successfully with this in mind. No research exists which has ever considered or developed these properties within a product successfully.

Other objects and advantages of the present invention will become apparent from the following description, wherein, by way of example, an embodiment of the present invention is disclosed.

SUMMARY OF THE INVENTION

According to the present invention, although this should be seen as limiting the invention in any way, there is provided a dental paste including an antibiotic both in free form and incorporated within a soluble calcium cement and a steroid in free form alone and incorporated within a slightly soluble calcium cement.

In a further form of the invention there is a provided a dental paste having:
  a first portion including an amount of a ground combination of a setting material and an antibacterial compound, wherein the antibacterial compound is incorporated into a matrix formed by the setting material; and
  a second portion including a free antibiotic and steroid and non-setting material,
  wherein the first and second portions are mixed together into a paste consistency.

In preference, the dental paste is a root filling material.

A method of treating a root canal, the method comprising administering to a patient in need of root canal therapy a dental paste including an antibiotic both in free form and incorporated within a soluble calcium cement and a steroid in free form alone.

A method of treating a root canal, the method comprising administering to a patient in need of root canal therapy a dental paste comprising:
  a first portion including an amount of a ground combination of at least partially set material and an antibacterial compound, wherein the antibacterial or anti-inflammatory or antibiotic compound is incorporated into a matrix formed by the partially set material. The at least partially set material is then finely ground to provide a non-setting filler base of the new paste. This is then combined with a second portion including a free antibiotic and steroid and non-setting material into a paste consistency.

A method of preparing a dental paste, the method including the steps of:
  combining a first portion of a settable material with at least one antibiotic and/or steroid or non-steroidal anti-inflammatory agent to form at least a partially set material-antibiotic paste;

all of the ingredients are mixed and allowed to set. The at least partially set material is then ground to form a powder; with the antibiotics, steroids or other specific pharmaceutical agents encapsulated within the set product. The powder forms a key basis of the new paste providing a means for the slow release of the encapsulated materials. As the outer calcium cement material dissolves it also releases the antibiotic/steroid and any non-steroidal components in a gradual and sustained manner. In the past it was believed that adding calcium hydroxide to an existing antibiotic/steroid paste would produce a slow release formula. This was shown to be false through our research, which clearly indicated the destruction of the steroid and antibiotic components. The lack of detection was incorrectly assumed to be due to their slow, sustained release.

Then combining the ground at least partially set settable material-antibiotic paste with a non-settable material to form a paste.

In preference, the settable material is at least a calcium cement compound.

In preference, the at least one of the calcium cement compound is selected from the group consisting of calcium sulphate, calcium phosphate, calcium silicate and calcium chloride.

In preference a steroidal or non-steroidal anti-inflammatory compound is included in the non-settable material along with an antibiotic or combination of antibiotics In preference, the antibiotic is 1-10% w/w.

In preference, the remaining calcium cement compound is 20-50% w/w.

In preference, the dental paste is a slow release dental paste.

In preference, the non-settable material is at least one inert non-setting material.

The term inert is used to include reference to bio-inactive materials.

In preference, the inert non-settable material is selected from the group consisting of liquids like water low molecular weight polyethylene glycol, glycols or any other liquid component typically used in paste formulations.

Zinc oxide may also be use as the inert non-setting filling material to make up the bulk of the paste. Zinc oxide has been utilised for decades The antibiotic can be of any kind and may be of multiple antibiotics in combination. These are reacted with the unset calcium cement and time is given for the calcium cement to set. The set cement is then ground to form a combination of calcium cement, which is impregnated with an antibiotic, steroid c or multiple antibiotics and other pharmaceutical agents.

DETAILED DESCRIPTION OF THE INVENTION

An antibiotic compound, or selection of antibiotic compounds, is mixed with a settable material such as a calcium cement compound, or any suitable dental cement material containing calcium can be used. This first mix is then allowed to at least partially set so that it can be ground to a powder. By being at least partially set, this means that the material has not become so hard that it is unable to be worked on, although if the material does fully set then it would simply require more work to grind the material, particularly if left to set into a single hard lump. The calcium cement compound is thus in the dihydrate form, allowing it at least partially set and encapsulate or at least substantially encapsulate the antibiotic(s).

In this manner there is a first setting of the cement material and the antibiotic materials to form an initial cement/antibiotic matrix, the antibiotic being now incorporated/encapsulated into the cement material and the combination is in the form of a powder.

The initial cement/antibiotic powder is then mixed with a second portion of materials, which includes liquids and gelling agents, which assist to form the paste. Identical percentages of those materials incorporated into the set components also applied to the second component to ensure consistency of concentration of ingredients across the range. Once incorporated within the paste, the antibiotic/calcium cement powder provides a source of calcium whilst maintaining an effective amount of antibiotic to avoid bacterial repopulation of the paste.

It further allows for an increased time-frame that the paste can be utilised by ensuring the antibiotic lasts longer. It provides reduced levels of cytotoxicity in comparison to calcium hydroxide pastes as there is reduced alkalinity. It provides a source of calcium ions to assist in the formation of hard tissue particularly important in cases where root formation is incomplete which antibiotic/steroid pastes do not.

The calcium cements can include and are not limited to calcium sulphate, calcium phosphate, calcium silicate or a combination of differing calcium salts or cements.

The antibiotics can be of any kind as it is not the type of antibiotic's which is crucial but rather its incorporation into a soluble calcium salt to prolong its activity within the root canal along with it being available in the free form for a more potent initial effect. The two methods together form a very effective method of providing excellent initial antibacterial properties more likely to be required at its initial application along with longer term preservative action to maintain a bacteria free paste.

Once a paste of suitable thickness is formed, it can be applied to the required area in any manner of ways as known to those skilled in the art. The radio-opaquing agent is added as a known means to help in the identification of the material when x-rays are being taken of patient's teeth.

An example of a formulation of the present invention is as follows:

| Ingredients | % w/w |
|---|---|
| Antibiotic | 5-10% overall including incorporation into calcium cement. |
| Calcium cement | 34% |
| Polyethylene glycol | 30% |
| Water | 20% |
| Silicon dioxide | 5% |
| Steroid | 1% |
| Radio-opaquing agent | 5% |

Observations have shown that the paste of the present invention provides a sustained release of calcium over a longer period of time and an improved stability and efficacy for the steroid and antibiotic compounds within the paste. This is of great benefit as it extends the working life of the paste in situ and thus provides greater benefit for the patient than is otherwise observed with currently used root canal dental pastes.

What is now apparent is that a long lasting source of calcium ions are available and when compared to the standard calcium hydroxide-based treatment approaches there is minimal cytotoxicity whilst maintaining similar free calcium ion release. In addition, the paste is long lasting and does not require replacement as often as the filler is impregnated with antibiotic sufficient to inhibit repopulation of the paste from bacteria.

The invention claimed is:

1. A root canal dental paste comprising:
    a first partially set portion comprising an amount of a ground combination of a calcium cement-based setting material and at least one antibiotic compound, wherein the at least once calcium cement-based setting material is selected from the group consisting of calcium sulphate, calcium phosphate, calcium chloride and calcium silicate, the at least one calcium cement material being in a dihydrate form; and
    a second portion comprising at least one inert non-settable material selected from the group consisting of zinc oxide, polyethylene glycol, and silicon oxide, and at least one antibiotic compound and/or at least one compound selected from the group consisting of steroidal and non-steroidal compounds, wherein the first partially set portion and second portion are subsequently combined to form a paste, and wherein the at least one antibiotic compound is incorporated into a matrix formed by the first partially set portion.

2. The dental paste of claim 1 wherein the concentration of antibiotic is 1-10% w/w.

3. The dental paste of claim 1 wherein the concentration of the at least one calcium cement material is 20-50% w/w.

* * * * *